United States Patent [19]
White et al.

[11] Patent Number: 5,366,609
[45] Date of Patent: Nov. 22, 1994

[54] BIOSENSING METER WITH PLUGGABLE MEMORY KEY

[75] Inventors: Bradley E. White, Indianapolis; Robert A. Parks, Springport; Paul G. Ritchie; Terry A. Beaty, both of Indianapolis, all of Ind.

[73] Assignee: Boehringer Mannheim Corporation, Indianapolis, Ind.

[21] Appl. No.: 73,316

[22] Filed: Jun. 8, 1993

[51] Int. Cl.$^5$ .................................................. G01N 27/26
[52] U.S. Cl. ...................... 204/403; 204/406; 204/407; 435/817
[58] Field of Search ................ 204/403, 406, 407; 435/817

[56] References Cited

U.S. PATENT DOCUMENTS

| | | | |
|---|---|---|---|
| 4,420,564 | 12/1983 | Tsuji et al. | 204/403 |
| 4,940,945 | 7/1990 | Littlejohn et al. | 324/438 |
| 4,975,647 | 12/1990 | Downer et al. | 204/403 |
| 4,999,582 | 3/1991 | Parks et al. | 204/406 |
| 5,053,199 | 10/1991 | Keiser et al. | 422/68.1 |
| 5,108,564 | 4/1992 | Szuminsky et al. | 204/403 |

FOREIGN PATENT DOCUMENTS

0471986A2 2/1992 European Pat. Off. .

*Primary Examiner*—John Niebling
*Assistant Examiner*—Bruce F. Bell
*Attorney, Agent, or Firm*—Perman & Green

[57] ABSTRACT

A biosensing meter is enabled to receive a sample strip that includes a sample well with an analyte reactant therein and electrodes in contact therewith. The biosensing meter includes an excitation supply for supplying potentials to a sample strip electrode. A sense amplifier is also provided for connection to another electrode of an inserted sample strip and produces an output signal indicative of sensed currents when an analyte containing fluid is present in the strip's sample well. A pluggable memory key is insertable into the meter and includes a plurality of stored parameter values and procedure routines that control operations of the meter. A microprocessor is responsive to a procedure routine and parameter values accessed from the pluggable memory key to cause the excitation supply to apply a plurality of potentials for preset durations, both the values of the potentials and the time duration of their application determined from parameter values derived from the memory key. The microprocessor controls the sense amplifier to provide a plurality of signal outputs over a predetermined duration, the sense amplifier being operated under control of specific parameter values derived from the pluggable memory key. Replacement of a pluggable memory key with a memory key containing alternative procedures and parameters enables the biosensing meter to carry out substantially modified test procedures without a requirement for modification of the structure of the meter.

12 Claims, 6 Drawing Sheets

BIOSENSING METER WITH PLUGGABLE MEMORY KEY

FIELD OF THE INVENTION

This invention relates to biosensing meters for determining the presence of an analyte in a biological sample, and, more particularly, to a biosensing meter whose operation is controlled by data accessed from a removably pluggable memory module.

BACKGROUND OF THE INVENTION

Biosensing instruments used for the detection of analyte levels in blood (such as glucose and cholesterol) often employ disposable sample strips that include a well or reaction zone for receiving a blood sample. A microprocessor/read only memory (ROM) combination controls the operation of the biosensing instrument and enables it to execute various procedures to obtain a desired analyte reading. However, if the algorithm/procedure used to determine the analyte level is improved, supplanted, or otherwise changed, and it is desired to update the meter to employ the improved procedure, a redesign of the meter is generally the result. In addition, meters previously sold to customers are obsoleted—even though the improved procedure may merely require the substitution of one memory chip for another memory chip.

Prior art biosensing meters have employed both current sensing and reflectance techniques for detection of analyte levels in blood samples. In reflectance-type meters, variations in sample strip test chemistries were accommodated through the provision of a removable memory chip that carried information regarding a specific batch of sample strips. In U.S. Pat. No. 5,053,199 to Keiser et al. and assigned to the same assignee as this application, a biosensing meter of the reflectance type is provided with a pluggable, programmable ROM that contained information pertinent to the optical characteristics of a particular batch of sample strip test chemistries. Such information enables the user to obtain an analyte reading without being required to mechanically insert calibration information (that had been previously provided with different packages of sample strips). That calibration information includes a table or set of tables that convert a reading obtained from an optical sensor to an analyte concentration value. Keiser et al. enables such calibration information to be directly loaded from the ROM to the meter.

In U.S. Pat. No. 4,975,647 to Downer et al., an analytical machine (e.g., a chromatograph) that employs consumable fluids is provided with a facility to receive a pluggable memory module. That memory module contains information concerning the timing of calibration operations, information identifying the fluids container, information identifying a class of analyzers with which the fluids container is usable, and information identifying the concentration of the fluids. Such information is then used to manage the frequency and times at which the instrument is calibrated and to further assure that a fluid pack is mated with an instrument that can properly utilize the fluids. In one example, Downer et al. describe a blood analyzer with a pluggable memory module that identifies the type of blood analyzer with which the fluid pack is intended to be used; the manufacturing lot of the fluid pack; a serial number uniquely identifying the fluid pack; concentrations of an electrolyte solution in the fluid pack; calibration zone times; "slippage" variables and a conventional two byte cyclic redundancy check (CRC) word.

The prior art includes further disclosures of biosensing instruments that employ disposable sample strips. In U.S. Pat. No. 5,108,564 to Szuminsky et al., a biosensing instrument is disclosed that measures glucose concentrations in blood. The instrument depends upon a reaction wherein glucose, in the presence of an enzyme, catalyzes a reaction of potassium ferricyanide to potassium ferrocyanide. After the reaction has completed, a voltage is applied across a reaction zone and causes a reversal of the reaction with an accompanying generation of a small, but measurable current. That current is termed the Cottrell current and, in dependence upon the concentration of glucose in the reaction zone, follows a predetermined curve during the reverse reaction. A reading of the Cottrell current is converted into an indication of glucose concentration. The instrument also senses an impedance across the reaction zone and determines when a blood sample has been emplaced therein by detecting a sudden change in current flow. At such time, an incubation period is commenced, followed by application of a potential across the reaction zone and measurement of the Cottrell current.

European Patent Application 0 471 986 A2 of Tsutsumi et al. discloses a blood glucose measurement system that employs disposable sample strips. The Tsutsumi et al. system detects the presence of a blood sample by sensing a resistance across a pair of electrodes. It further employs a plurality of sample-like strips, each having a specific resistance value which distinguishes it from other strips. Each of those strips has a particular application, i.e., for use during an adjustment mode of the instrument, during an error compensation mode, during a calibration mode, etc.

U.S. Pat. No. 4,999,582 to Parks et al., assigned to the same Assignee as this application, describes a biosensor electrode excitation circuit for determining if a sample strip has been properly inserted into a meter and if at least one electrode on the sample strip exhibits a proper level of contact resistance.

U.S. patent application Ser. No. 07/451,309, filed Dec. 15, 1989, to White, entitled "Biosensing Instrument and Method" and assigned to the same assignee as this application, teaches a biosensing instrument which employs the "Cottrell" curve relationship to determine glucose concentrations. In that instrument, current flow is proportional to the concentration of an analyte in the test cell; however, when something is amiss in the test cell, the current that results may bear no relationship whatever to analyte concentration. White indicates that a relationship exists that enables a determination to be made whether current flow through a reaction zone is, in fact, following the Cottrell relationship. More specifically, the ratio of the square roots of succeeding sample times, for all analyte concentration curves, to inversely approximate the ratio of the measured Cottrell currents at those same sample times. If over succeeding time periods, the ratios are equal (within limits), the measurement system is properly following the Cottrell relationship. If the ratios found are not equal, the measurement is disregarded.

U.S. Pat. No. 4,940,945 to Littlejohn et al. describes an interface circuit for use in a biochemical sensing instrument. A disposable cartridge is employed that includes a pair of electrodes across which resistance measurements are taken. Circuitry is disclosed for sensing the presence of a fluid sample by an initial resistance measurement, and also the level of fluid in the cartridge.

U.S. Pat. No. 4,420,564 to Tsuji et al. describes a blood sugar analyzer that employs a reaction cell having a fixed enzyme membrane sensor and a measuring electrode. The Tsuji et al. system includes several fail-/safe procedures, one to determine that the reaction is taking place within specifically defined temperature limits and a second to determine that the reaction current remains within a predetermined range.

While the above prior art indicates that it is known to employ pluggable read only memories for insertion of data regarding characteristics of disposable sample strips (and/or fluid packs), none addresses the problem of enabling a biosensing meter to adapt to substantially revised test protocols and procedures without the need for redesign of the electronics or meter.

Accordingly, it is an object of this invention to provide a biosensing meter with a pluggable memory module that enables substantial reconfiguration of test procedures and parameters employed by the meter.

It is another object of this invention to provide a biosensing meter with a pluggable memory module that enables threshold potentials, test times, delay periods and other pertinent test procedures and constants to be inserted and/or altered.

It is yet another object of this invention to provide a biosensing meter with a pluggable read only memory wherein data read from the read only memory at sequential times during the use of the meter enables a determination to be made as to whether the read only memory has been switched during a test procedure.

SUMMARY OF THE INVENTION

A biosensing meter is enabled to receive a sample strip that includes a sample well with an analyte reactant therein and electrodes in contact therewith. The biosensing meter includes an excitation supply for supplying potentials to a sample strip electrode. A sense amplifier is also provided for connection to another electrode of an inserted sample strip and produces an output signal indicative of sensed currents when an analyte containing fluid is present in the strip's sample well. A pluggable memory key is insertable into the meter and includes a plurality of stored parameter values and procedure routines that control operations of the meter. A microprocessor is responsive to a procedure routine and parameter values accessed from the pluggable memory key to cause the excitation supply to apply a plurality of potentials for preset durations, both the values of the potentials and the time duration of their application determined from parameter values derived from the memory key. The microprocessor controls the sense amplifier to provide a plurality of signal outputs over a predetermined duration, the sense amplifier being operated under control of specific parameter values derived from the pluggable memory key. Replacement of a pluggable memory key with a memory key containing alternative procedures and parameters enables the biosensing meter to carry out substantially modified test procedures without a requirement for modification of the structure of the meter.

DETAILED DESCRIPTION OF THE INVENTION

Figure 1:
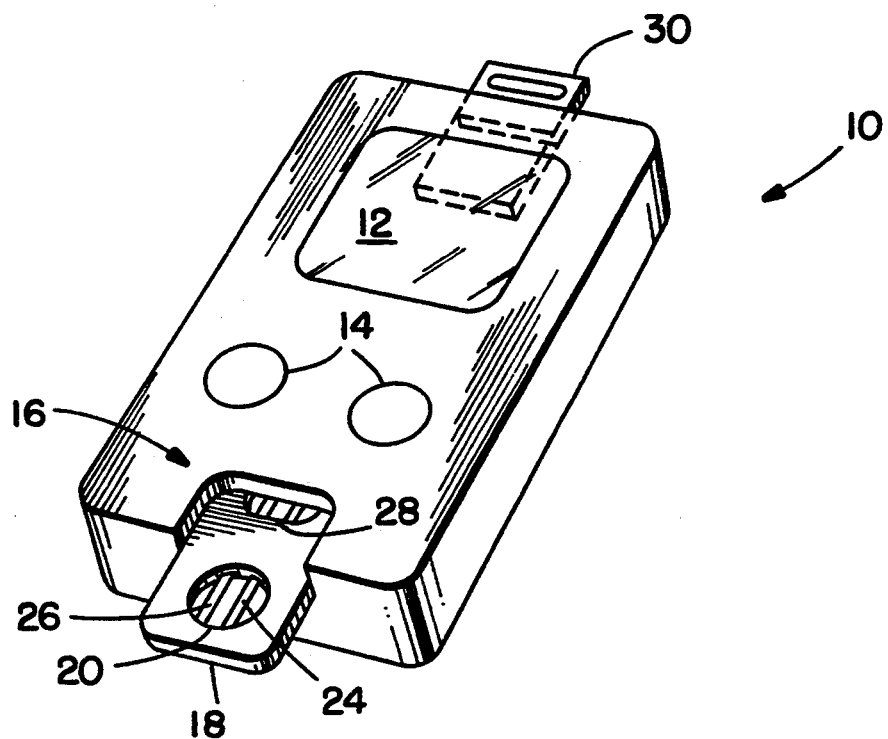
FIG. 1 is a perspective view of a biosensing meter incorporating the invention.

Referring now to FIG. 1, a biosensing meter 10 includes a display 12, control buttons 14 and a slot 16 for receiving a disposable sample strip 18. Sample strip 18 contains a well 20 (i.e., a reaction zone) that encompasses a pair of conductive electrodes 24 and 26. A layer (not shown) of enzymatic reactants overlays electrodes 24 and 26 in well 20 and provides a substrate on which an analyte-containing fluid sample may be emplaced. Disposable sample strip 18 has an opening 28 at its distal end that exposes electrodes 24 and 26 and renders them available for electrical connection with biosensing meter 10. A pluggable ROM key 30 mates with an electrical receptacle within meter 10 so as to be in electrical communication with control circuitry internal thereto.

Figure 2:
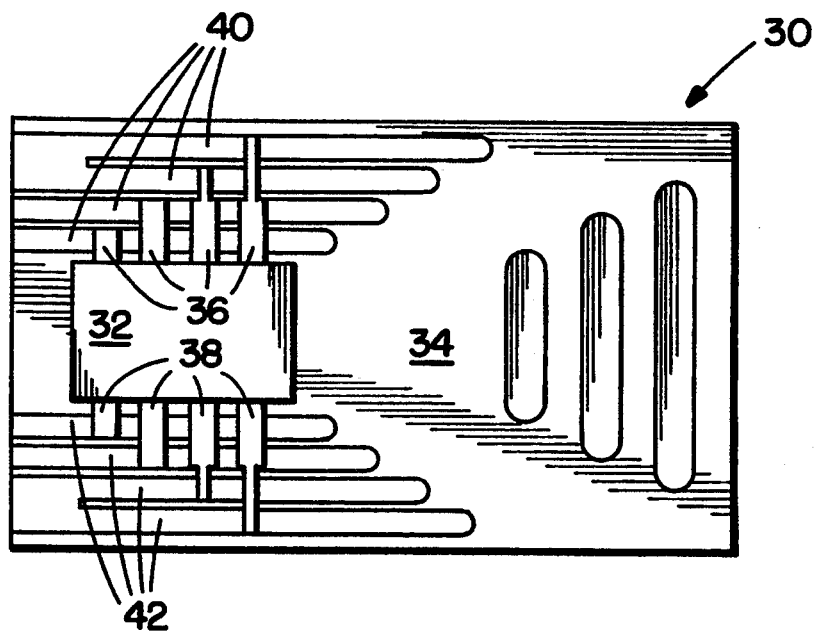
FIG. 2 is a plan view of a pluggable read only memory key for controlling the operation of the biosensing meter shown in FIG. 1.

ROM key 30 is shown in FIG. 2 and includes a programmable ROM chip 32 that is adherent to a supporting surface 34. A plurality of leads 36 and 38 emanate from ROM chip 32 and terminate, respectively, at grooves 40 and 42. Substrate 34 is insulating and provides a support for chip 32. Grooves 40 and 42 provide insulating guides that assure that electrical contacts within meter 10 are channeled to make contact with leads 36 and 38 and do not become electrically shorted.

When ROM key 30 is inserted into meter 10, a plurality of flexible contacts internal to meter 10 make connection with leads 36 and 38 and enable a microprocessor within meter 10 to access data stored in ROM chip 32.

Figure 3:
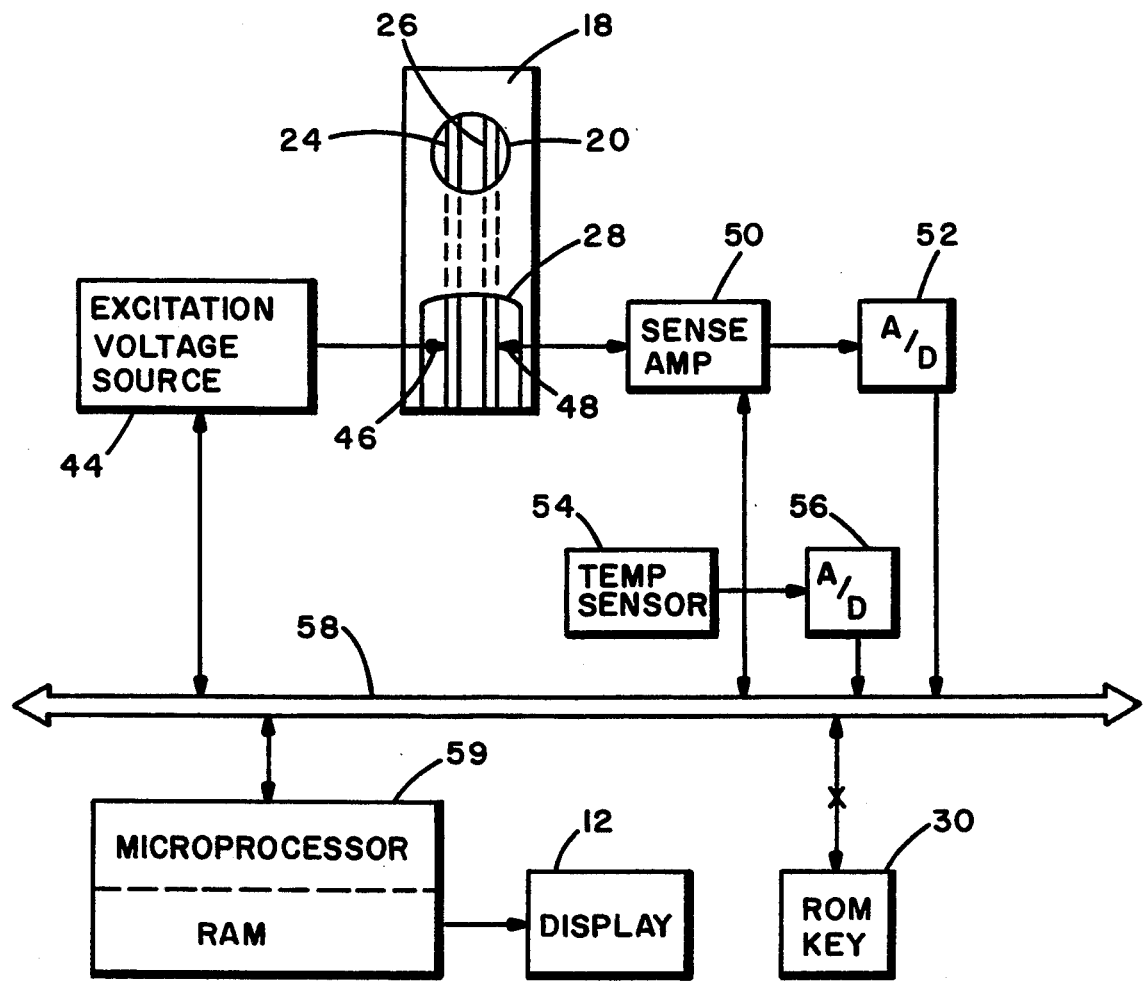
FIG. 3 is a block diagram of circuitry contained within the biosensing meter shown in FIG. 1.

Referring to FIG. 3, a schematic is shown of circuitry within biosensing meter 10, and illustrates a disposable sample strip 18 inserted into slot 16. An excitation voltage source 44 provides a variable voltage to a contact 46 that makes connection with electrode 24 on disposable sample strip 18. A contact 48 enables a potential appearing on electrode 26 to be fed to a sense amplifier 50 whose output, in turn, is fed to an analog-to-digital converter (A/D) 52. A temperature sensor 54 is positioned within meter 10 and also provides its output to an A/D converter 56. The outputs from A/D converters 52 and 56 are applied to a bus 58 which provides communications between modules contained within biosensing meter 10.

A microprocessor 59, with a display unit 12, provides overall control of the operation of biosensing meter 10 in combination with data read from ROM key 30. ROM key 30 is pluggable into biosensing meter 10 and contains non-volatile memory that includes constants and other data required to carry out analyte-determination procedures. In general, a ROM key 30 will accompany each batch of disposable sample strips 18 and will contain constants and procedure code that enable meter 10 to adjust its measurement parameters to match the specific batch characteristics of disposable sample strips 18. Further, ROM key 30 will also contain a large number of additional variable values that control the operation of microprocessor 59 in performing the actual analyte determination tests. Those variables will be discussed in detail below.

Excitation voltage source 44 and sense amplifier 50 receive their commands from microprocessor 59 via bus 58. Excitation voltage source 44 responds to those commands by applying various levels of excitation potential to electrode 24 of sample strip 18. Sense amplifier 50 is controlled to have two different levels of gain so as to avoid a saturation condition upon an initial application of an excitation voltage to sample strip 18.

As an example, it will be assumed that the analyte-containing sample is a drop of blood that is being subjected to a glucose determination. A disposable sample strip for a glucose determination will include, in well 20, the following reactants: an enzyme, an electrolyte, a mediator, film formers, and a buffer. For instance, the enzyme may be glucose oxidase or glucose dehydrogenase; the buffer may be organic or inorganic; the electrolyte may be potassium chloride or sodium chloride; the mediator is preferably potassium ferricyanide and the film formers comprise gelatin and propiofin. (If the test cell is to be employed for a cholesterol concentration determination, the enzyme would preferably be cholesterol oxidase, with or without a cholesterol esterase additive. The buffer would be preferably inorganic and would include an electrolyte such as potassium chloride or sodium chloride. In this case two mediators would be used, (i.e. ferricyanide and quinones, and would be placed in the gelatin film as indicated above.)

As the chemistries employed to make such analyte determinations are known in the art, they will not be described in significant detail. Suffice to say that a glucose determination is made by initially emplacing in well 20, a sample of blood. The glucose within the sample causes a forward reaction of potassium ferricyanide to potassium ferrocyanide. The forward reaction proceeds to completion during an incubation period. A subsequent application of an excitation voltage to excitation electrode 24 in disposable sample strip 18 will see the creation of a small current at sense electrode 26 that results from a reverse reaction of potassium ferrocyanide back to potassium ferricyanide. The flow of electrons during the reverse reaction is sensed and measured at a number of points so as to enable a determination to be made that the reaction is both following a Cottrell curve and to further determine the level of the Cottrell curve. That level is indicative of the glucose concentration. The resultant glucose value, is thereafter corrected to take into account ambient temperature.

As above indicated, the operation of a biosensing meter 10 is substantially controlled by data contained in ROM key 30. ROM key 30 will contain a variety of data values that are critical to the proper operation of meter 10. Those values encompass measurement delay times, an incubation time, the number of measurements to be taken during a measurement period, various thresholds against which voltage levels are to be compared, values of excitation voltage levels to be applied to sample strip 18 during a test procedure, glucose value conversion factors, and a variety of failsafe test threshold values. In addition, ROM key 30 may contain either a portion of or the entire code listing that controls the procedures of meter 10 so that, by substitution of a new ROM key, test procedures performed by meter 10 can be altered accordingly.

Because the amount of random access memory (RAM) contained within microprocessor 59 is limited, data from ROM key 30 is loaded into RAM by microprocessor 59 only on an as needed basis, after which it is discarded, with new data taking its place. In the forthcoming description of the operation of meter 10, values accessed from ROM key 30 will be noted by a (key) immediately thereafter in the text.

Turning to FIGS. 3–6, the operation of meter 10 in determining a glucose value will be described. Initially, microprocessor 59 determines that a sample strip is properly inserted and that its excitation and sense electrodes 24 and 26 exhibit proper electrode continuities. This operation is described in detail in copending U.S. patent application, Ser. No. 08/073178 of Bradley White et al , entitled "Biosensing Meter with Disposable Sample Strips and Check Strips for Meter Quality Determinations", filed on even date herewith (attorney docket 058-924262-NA). The disclosure of the White et al., patent application is incorporated herein by reference.

Figure 4:
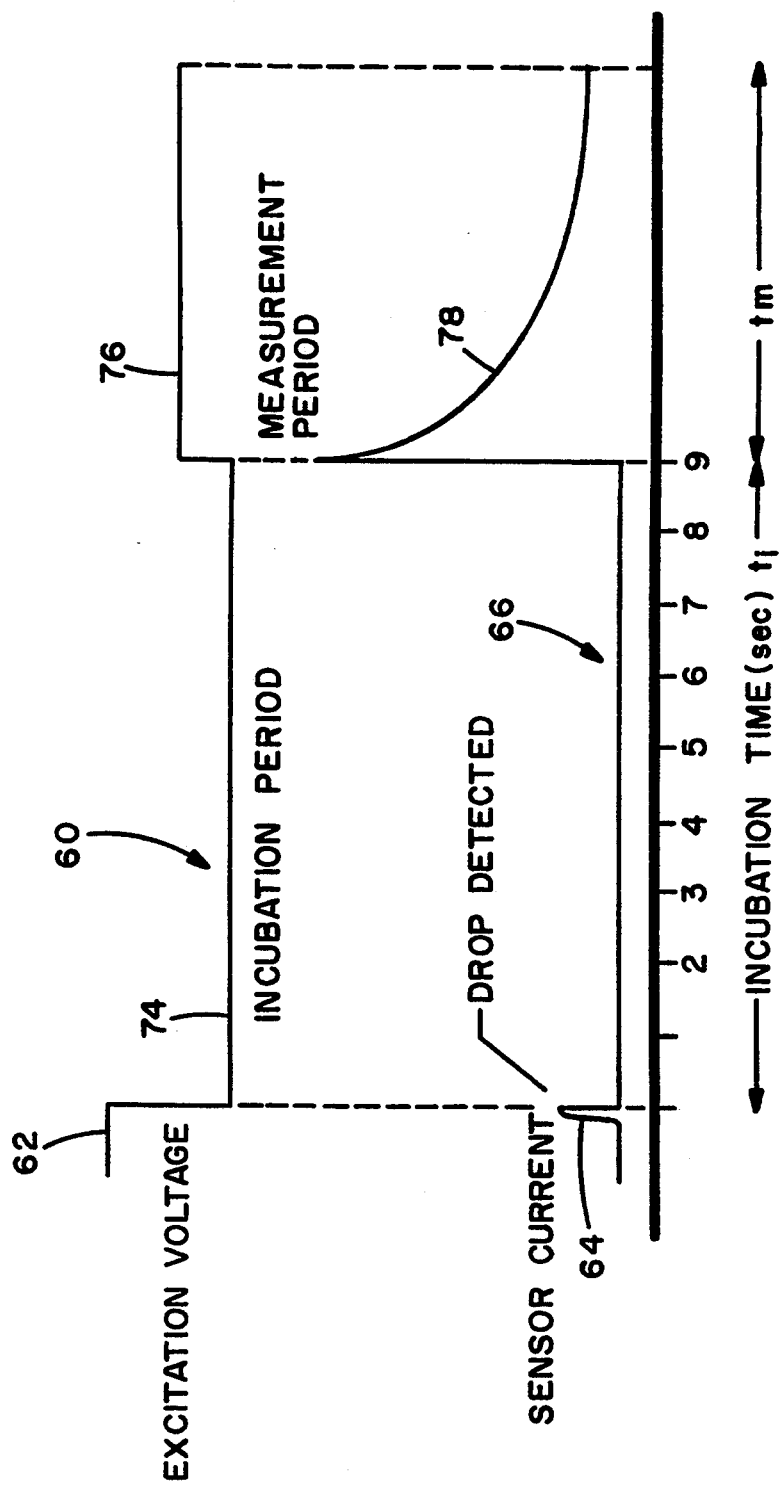
FIG. 4 is a waveform diagram illustrating an excitation voltage applied to an excitation electrode of a sample strip used with the biosensing meter of FIG. 1, and a resulting sense current determined from a sense electrode on the sample strip.
Figure 5:
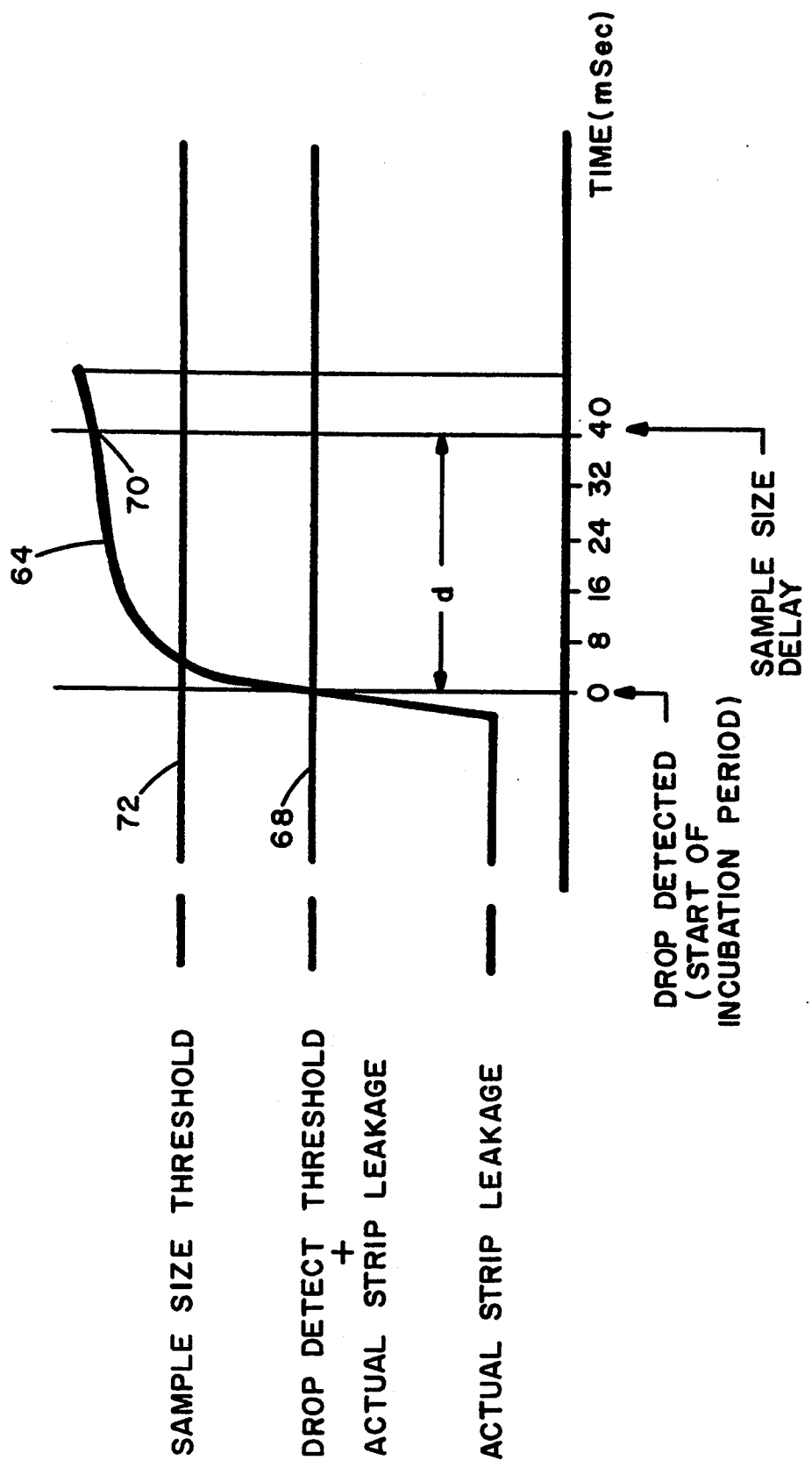
FIG. 5 is an expanded view of the sense current waveform that occurs when a drop of analyte is initially detected.

Microprocessor 59 next (before a drop of blood is placed in well 20), causes excitation voltage source 44 to apply an excitation voltage level 62 (key) (FIG. 4) to excitation electrode 24. The initial voltage level 62 (key) enables a measurement to be made of leakage current between excitation electrode 24 and sense electrode 26. If the leakage current (sensed by sense amplifier 50 and fed to microprocessor 59 via A/D converter 52) is found to be less than a threshold (key), microprocessor 59 indicates via display 12, that the user may apply a drop of blood to well 20. Upon application of the drop of blood, an immediate drop in resistance, (i.e., an increase in current) is sensed between electrodes 24 and 26 by sense amplifier 50. The resulting output from sense amplifier 50 is indicated as pulse 64 of signal trace 66 in FIG. 4. An expanded view of pulse 64 is shown in FIG. 5.

As pulse 64 passes through a first threshold level 68, microprocessor 59 determines that a drop of blood has been detected. The level of threshold 68 is at a low level so as to rapidly detect when a sample strip 18 is dosed with a blood sample and to thereby clearly indicate the commencement of an incubation period $t_i$ (FIG. 4). Threshold level 68 is computed by microprocessor 59 by adding a drop detect threshold (key) to the actual measured strip leakage.

Upon pulse 64 passing through threshold 68, a time delay d (key) is commenced, at the termination of which a second measurement is taken of waveform 64 (at time 70). Time delay d enables the drop of blood to entirely wet the enzyme layer within well 20. If the voltage sensed at time 70 is below a sample size threshold 72 (key), the test is aborted as the volume of blood is determined to be insufficient to assure complete hydration of the enzymatic reactants within well 20. By contrast, if the current sensed at time 70 exceeds sample size threshold 72 (key), the test is permitted to continue.

Next, microprocessor 59 causes the excitation voltage from excitation voltage source 44 to be removed. Trace 74 is the "incubation" time $t_i$ (key) and extends for a sufficient period of time to enable an enzymatic reaction to occur between a blood drop and the enzymes in well 20.

At the termination of incubation time $t_i$, a further excitation voltage (trace 76, FIG. 4) (key), is applied to excitation electrode 24 causing a reverse reaction in well 20. An exponentially decreasing current (trace 78 in FIG. 4) is sensed at sense electrode 26 by sense amplifier 50.

Figure 6:
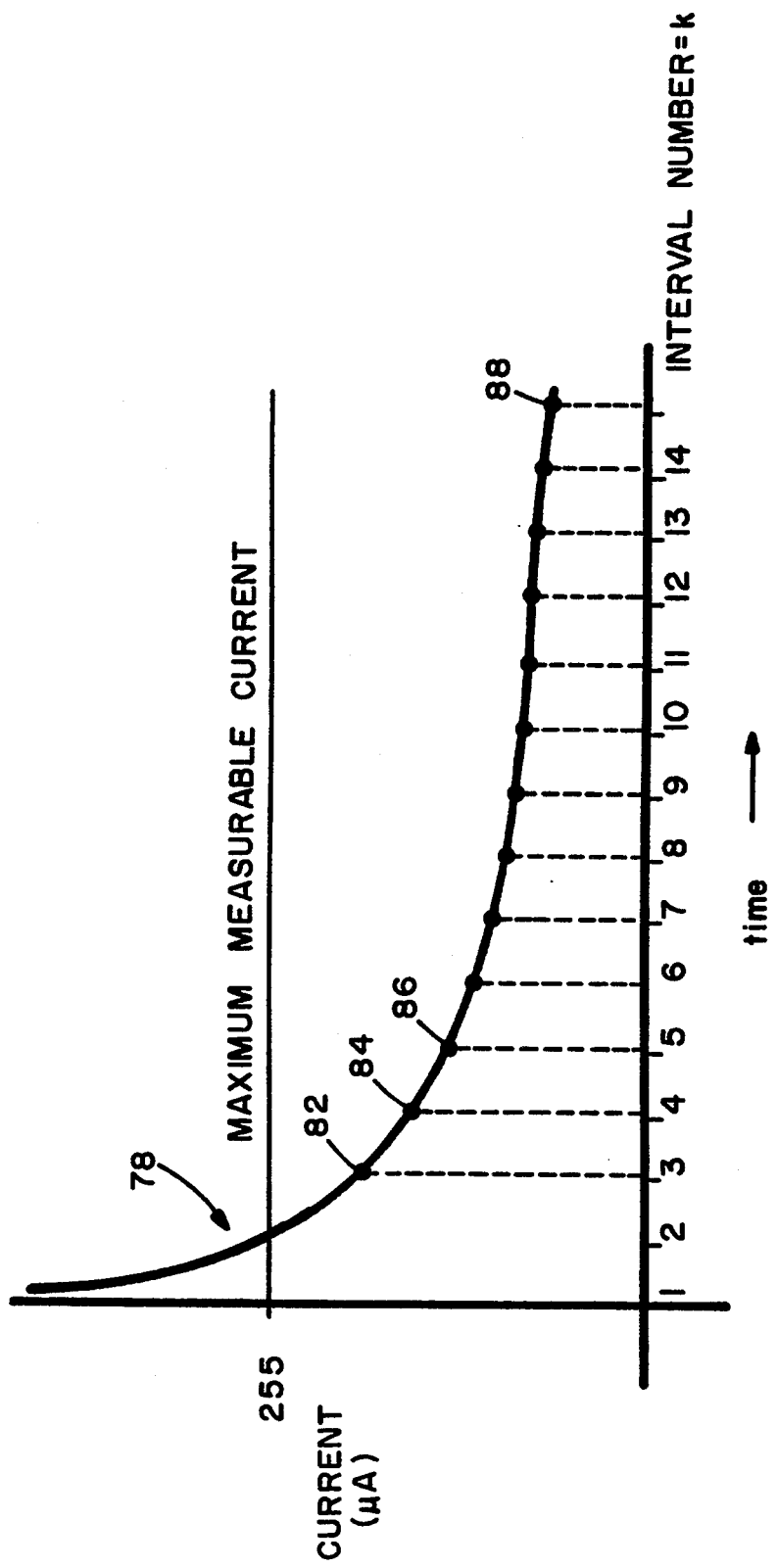
FIG. 6 is an expanded view of a plurality of measured currents detected during the measurement period, which currents follow an expected Cottrell relationship.

FIG. 6 is an enlarged showing of trace 78 (sense current is plotted against elapsed time) and illustrates the classic Cottrell relationship exhibited by current flow during the reverse reaction. Trace 78 is either displaced upwardly or downwardly in the plot of FIG. 66 depending upon glucose concentration. During the period of trace 78, microprocessor 59 causes a plurality of current measurement values to be sampled, each value taken a time interval k (key) apart. The total number of measurement intervals (e.g. fourteen) is a value also derived from ROM key 30.

The sense current measurements enable a glucose determination to be made and are used to assure that trace 78 is, in fact, following the Cottrell relationship. To assure that trace 78 is of the proper shape, a number of fail/safe determinations are made, based upon the current measurements (e.g., 82, 84, 86, 88 etc.). In each instance, threshold values (key) are employed to determine whether the respective current measurements from trace 78 are within predefined limits. Details of each of the fail safe calculations are described in co-pending U.S. patent application Ser. No. 08/073180 (Attorney Docket 058-924214-NA) of White et al. and entitled "Biosensing Meter with Fail/Safe Procedures to Prevent Erroneous Indications". The disclosure of the aforesaid U.S. patent application is incorporated herein by reference.

As shown in FIG. 6, fourteen intervals between measurements result from both a measurement interval count and an interval value derived from ROM key 30. A further delay measurement interval value is also derived from ROM key 30 and represents a count of a number of measurement intervals during which current measurements are inhibited after reapplication of excitation potential 76 to excitation electrode 24.

Figure 7:
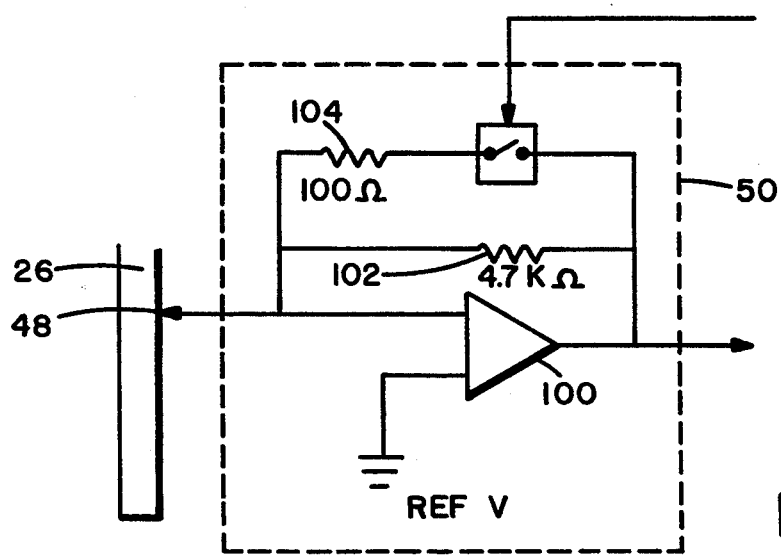
FIG. 7 is a circuit diagram of a sense amplifier whose gain state is controlled in accordance with data read from the pluggable read only memory key shown in FIG. 2.

In FIG. 7, a circuit diagram is shown of sense amp 50 and includes an operational amplifier 100 having an input connected via contact 48 to sense electrode 26. A feedback resistance 102 provides normal gain control for operational amplifier 100 and is shunted by a much lower resistance 104 and a switch 106. During the delay measurement interval (key), microprocessor 59 causes switch 106 to be closed thereby shunting amplifier 100 with resistor 104. This action prevents saturation of amplifier 100 during the period when the Cottrell current exceeds a maximum measurable current level (key). Subsequent to the delay measurement time, microprocessor 59 causes switch 106 to open so that operational amplifier 100 exhibits its normal gain characteristic and enables measurements 82, 84, etc. to be taken.

Subsequent to the Cottrell currents being recorded and stored, meter 10 proceeds to determine a glucose concentration by performing conversions of current values to glucose values from a calibration curve defined by values in ROM key 30; and then performing a temperature compensation correction procedure (key) in accordance with a temperature estimation procedure (key).

During the course of a glucose test, it is important that meter 10 not provide an erroneous indication to the user as such could cause a misadministration of medicine. If the user were to insert a ROM key 30 prior to the initiation of a glucose test and, sometime during the test remove ROM key 30 and insert another ROM key 30, erroneous results could occur.

Figure 8:
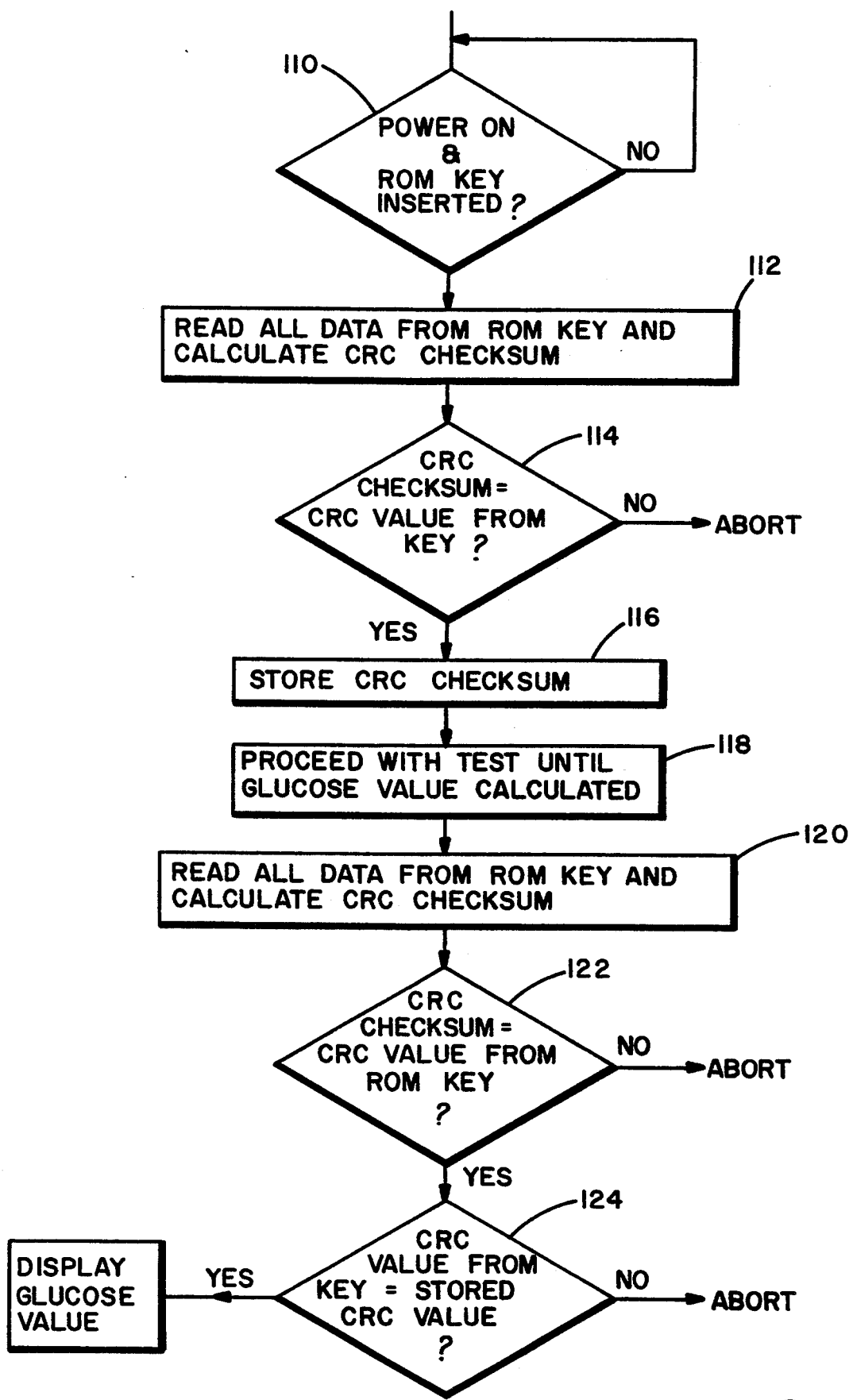
FIG. 8 is a high level flow diagram illustrating a procedure for determining whether a pluggable memory key has been changed during the course of a test procedure.

A procedure is shown in FIG. 8 for preventing such a switch of ROM keys. Data stored in ROM key 30 includes a cyclic redundancy check (CRC) checksum pertaining to all data stored therein. In the procedure shown in FIG. 8, after a power-on, meter 10 monitors whether a ROM key 30 has been inserted (decision box 110). If not, the monitoring continues. If yes, then all data is read from ROM key 30 and a CRC checksum is calculated therefrom (box 112), in the known manner. The calculated CRC checksum is then compared to a CRC value read from ROM key 30 and if the values are not identical, the test is aborted as there is an error in the data. If the values match, the CRC checksum is stored in RAM in microprocessor 59 and the test continues until a glucose value has been calculated (box 118). At this point, all data is again read from ROM key 30 and a CRC checksum is again calculated (box 120). That calculated CRC checksum is then compared to a CRC value read from ROM key 30 and if the values are not the same, an abort occurs (decision box 122). If an equality is found, then the most recently derived CRC checksum from ROM key 30 is compared against the stored CRC checksum (decision box 124) to determine if their values are equal. If yes, the glucose value is displayed. If no, the test aborts upon the assumption that ROM keys have been changed.

It should be understood that the foregoing description is only illustrative of the invention. Various alternatives and modifications can be devised by those skilled in the art without departing from the invention. For instance, while the invention has been described as including a meter with a pluggable key, the meter employing electrical signals passing through a reaction well for the determination of an analyte reaction, the pluggable key described hereinabove may also operate in conjunction with a meter that employs other reaction sensing implementalities, e.g., optical means. Accordingly, the present invention is intended to embrace all such alternatives, modifications and variances which fall within the scope of the appended claims.

What is claimed is:

1. A biosensing meter for receiving a sample strip that includes a sample well with an analyte reactant therein, said biosensing meter comprising:

sense means for outputting signals indicative of manifestations of a reaction in said sample well between an analyte-containing fluid and said analyte reactant;

pluggable memory key means for insertion into an electrical receptacle in said meter, said pluggable memory key means including a plurality of stored parameter values and procedure routine specifications that are employed in controlling execution of an algorithm performed by said meter that enables determination of an analyte concentration value, said procedure routine specifications including stored values from which time values can be determined for controlling said sense means during execution of said algorithm; and processor means coupled to said memory key means and responsive to parameter values and procedure routine specifications accessed from said pluggable memory key means, for controlling operation of said sense means in accordance with said algorithm and for calculating from signal outputs from said sense means a concentration value of an analyte in said analyte-containing fluid in said sample well.

2. The biosensing meter as recited in claim 1 wherein said pluggable key means further includes a procedure routine that, when executed by said processor means, enables execution of said algorithm.

3. The biosensing meter as recited in claim 1 wherein said pluggable key means stores a cyclic redundancy check value;

said processor means performing an initial test including reading out data from a said pluggable key means, calculating a cyclic redundancy check value therefor, comparing said calculated cyclic redundancy check value with a CRC value read from said pluggable key means to determine an identity therebetween and if such identity is established, storing said cyclic redundancy check value and enabling an analyte test to proceed, and at a conclusion of said analyte test, determining if said stored cyclic redundancy check value is equal to a CRC value read from said pluggable key means at said conclusion, whereby it is assured that a switch of memory key means has not occurred during a test procedure.

4. A biosensing meter for receiving a sample strip that includes a sample well with an analyte reactant therein and electrodes in contact therewith, said biosensing meter comprising:

excitation supply means for applying potentials to a first electrode on said sample strip upon insertion of said sample strip into said meter;

sense amplifier means for connection to a second electrode upon insertion of said sample strip into said meter, and for producing an output signal indicative of a current at said second electrode when an analyte containing fluid is present in said sample well;

pluggable memory key means for insertion into an electrical receptacle in said meter, said pluggable memory key means including a plurality of stored parameter values for controlling operations of said meter; and processor means coupled to said excitation supply means, sense amplifier means and memory key means, and wherein the processor means is responsive to parameter values accessed from said pluggable memory key means, to cause said excitation supply means to apply a plurality of voltages to said first electrode, each said voltage having a potential and being applied for a duration that is determined by said processor means from parameter values accessed from said pluggable memory key means, and to further control said sense amplifier means to provide a plurality of signal outputs over a set duration and to further calculate from said signal outputs a value equivalent to a concentration of an analyte in said analyte-containing fluid in said sample well, all in conformance with parameter values accessed from said memory key means.

5. The biosensing meter as recited in claim 4 wherein said pluggable memory key means further stores procedure routines for further controlling operations of said meter, said procedure routines employed by said processor means in determining analyte concentration.

6. A biosensing meter for receiving a sample strip that includes excitation and sense electrodes and a sample well bridging thereacross, said sample well including an analyte reactant, said biosensing meter comprising:

excitation supply means for applying potential to an excitation electrode upon insertion of a sample strip into said meter;

sense amplifier means for connection to a sense electrode upon insertion of a sample strip into said meter, and for producing an output signal indicative of a current at said sense electrode when an analyte containing fluid is present in said sample well;

pluggable memory key means for insertion into an electrical receptacle in said meter, said memory key means including a plurality of stored parameter values for controlling operations of said meter; and processor means coupled to said excitation supply means, sense amplifier means and memory key means, for causing said excitation supply means to apply to said excitation electrode first and second excitation potentials for first and second periods, respectively separated by an incubation period, and for further causing said sense amplifier means, during said second period, to provide a number of signal outputs indicative of sensed currents, values of said first and second excitation potentials and the number of signal outputs from said sense amplifier means controlled by parameter values accessed from said memory key means.

7. The biosensing meter as recited in claim 6 wherein said pluggable memory key means further includes threshold voltage values for enabling said processor means to determine that an amount of analyte containing fluid is present in said sample well and that a leakage current between said excitation electrode and sense electrode does not exceed a preset value.

8. The biosensing meter as recited in claim 7 wherein said pluggable key means further includes an elapsed time value that said processor means accesses and employs to control a duration of said incubation period.

9. The biosensing meter as recited in claim 7 wherein said pluggable memory key means further stores procedure routines for further controlling operations of said meter, said procedure routines employed by said processor means in determining analyte concentration.

10. A biosensing meter for determining a concentration of an analyte in a biological sample, said meter adapted to connect to a disposable sample strip that includes said biological sample in contact with an analyte reactant resident on said sample strip, said meter controllable to perform a plurality of tests, said meter comprising:

memory key means pluggably inserted into an electrical receptacle in said meter, said memory key means storing a plurality of parameters for controlling said tests and further storing a Cyclic Redundancy Check value;

processor means including read/write memory for controlling operation of said meter in conjunction with parameters received from a said memory key means, said processor means performing an initial test including reading out data from a said memory key means, calculating a cyclic redundancy check value therefor, comparing said calculated cyclic redundancy check value with a CRC value read from said key to determine an identity therebetween and if such identity is established, storing said cyclic redundancy check value and enabling an analyte test to proceed, and at a conclusion of said analyte test, determining if said stored CRC value is equal to a cyclic redundancy check value read from said memory key means at said conclusion, whereby it is assured that a switch of memory key means has not occurred during a test procedure.

11. The biosensing meter as recited in claim 10 wherein said processor means, at the conclusion of an analyte test, performs said initial test to assure that a cyclic redundancy check value calculated from data read from said memory key means at such time matches a cyclic redundancy check value read from said memory key means, as well as matching said stored cyclic redundancy check value.

12. A biosensing meter for receiving a sample strip that includes excitation and sense electrodes and a sample well bridging thereacross, said sample well including an analyte reactant, said biosensing meter comprising:

excitation supply means for applying potential to an excitation electrode to an inserted sample strip;

sense amplifier means for connection to a sense electrode upon insertion of a said sample strip into said meter, and for producing an output signal indicative of a current at said sense electrode when an analyte containing fluid is present in said sample well;

feedback means for controlling gain of said sense amplifier means;

pluggable memory key means for insertion into an electrical receptacle in said meter, said memory key means including a plurality of stored parameter values for controlling operations of said meter; and processor means coupled to said excitation supply means, sense amplifier means, feedback and memory key means, for causing said excitation supply means to apply to said excitation electrode first and second excitation potentials for first and second periods, respectively separated by an incubation period, and for causing said sense amplifier means to produce over N intervals, output values indicative of sensed currents during said second period, and for causing said feedback means to alter gain of said sense amplifier means from a low level to a higher level only after passage of a preset number of said N intervals, the value of N and said preset number desired from values read from said memory key means.

* * * * *